United States Patent
Insall et al.

(10) Patent No.: US 6,319,283 B1
(45) Date of Patent: Nov. 20, 2001

(54) TIBIAL KNEE COMPONENT WITH A MOBILE BEARING

(75) Inventors: John Insall, New York, NY (US); Audrey Patmore, Warsaw, IN (US); Christopher McLean, Warsaw, IN (US); Linggawati Tanamal, Warsaw, IN (US); Clayton R. Miller, Bremen, IN (US)

(73) Assignee: Bristol-Myers Squibb Company, New York, NY (US)

(*) Notice: Subject to any disclaimer, the term of this patent is extended or adjusted under 35 U.S.C. 154(b) by 0 days.

(21) Appl. No.: 09/346,850

(22) Filed: Jul. 2, 1999

(51) Int. Cl.$^7$ .................................................. A61F 2/38
(52) U.S. Cl. ............................... 623/20.33; 623/20.24; 623/20.29; 623/20.32
(58) Field of Search ................ 623/20.33, 20.32, 623/20.24, 20.29

(56) References Cited

U.S. PATENT DOCUMENTS

| | | |
|---|---|---|
| 4,085,466 | 4/1978 | Goodfellow et al. . |
| 4,094,017 | 6/1978 | Matthews et al. . |
| 4,136,405 | 1/1979 | Pastrick et al. . |
| 4,216,549 | 8/1980 | Hillberry et al. . |
| 4,219,893 | 9/1980 | Noiles . |

(List continued on next page.)

FOREIGN PATENT DOCUMENTS

| | | | |
|---|---|---|---|
| 0 472 475 A2 | 7/1991 | (EP) | ................ A61F/2/38 |
| 0 498 586 A1 | 1/1992 | (EP) | ................ A61F/2/38 |
| 0 519 872 A1 | 6/1992 | (EP) | ................ A61F/2/38 |
| 0 592 750 B1 | 12/1992 | (EP) | ................ A61F/2/38 |
| 0 670 151 A2 | 1/1995 | (EP) | ................ A61F/2/38 |

(List continued on next page.)

OTHER PUBLICATIONS

The Mechanical Testing of a Sliding Meniscus Knee Prosthesis; R.J. Minns, B.Eng., M.Sc., Ph.D., J. Campbell, CH.B., M.Ch. (Ortho), FRCS; Clinical Orthopaedics; Nov.–Dec. 1978, vol. 137; pp. 268–275.

S–ROM® Modular Total Knee System; Joint Medical Products Corp; 1993.

TRA™ Knee System Design Rationale; Nov. 1996; pp.1–23.

New Jersey LCS® Total Knee System; DePuy; 1994.

SAL Self–Aligning Total Knee Replacement; Protek.

Difficulties With Bearing Dislocation and Breakage Using a Movable Bearing Total Knee Replacement System; James K. Weaver, M.D., Robert S. Kerkash, M.D., A. Seth Greenwald D. Phil. (Oxon); Clinical Orthopaedics and Related Research; Number 290; pp 244–252; 1993 J. B. Lippincott Company.

(List continued on next page.)

*Primary Examiner*—David J. Isabella
*Assistant Examiner*—Urmi Chattopadhyay
(74) *Attorney, Agent, or Firm*—Todd A. Dawson (57) ABSTRACT

An orthopaedic knee component for implanting within a proximal tibia includes a tibial tray with a proximal tibial plateau and a projection extending generally orthogonal to the tibial plateau. The tibial tray also includes a distally extending stem. A bearing is coupled with the tibial plateau and has an articular bearing surface for engagement with a femoral component. The bearing is rotationally movable between a first rotational limit and a second rotational limit about an axis extending generally orthogonal to the tibial plateau. The bearing has a backing surface engaging the tibial plateau which is sized and shaped such that the backing surface is substantially entirely supported by the tibial plateau at any position during rotational movement between the first rotation limit and the second rotational limit.

12 Claims, 6 Drawing Sheets

U.S. PATENT DOCUMENTS

| | | |
|---|---|---|
| 4,224,696 | 9/1980 | Murray et al. . |
| 4,224,697 | 9/1980 | Murray et al. . |
| 4,257,129 | 3/1981 | Volz . |
| 4,262,368 | 4/1981 | Lacey . |
| 4,301,553 | 11/1981 | Noiles . |
| 4,309,778 | 1/1982 | Buechel et al. . |
| 4,470,158 | 9/1984 | Pappas et al. . |
| 4,586,933 | 5/1986 | Shoji et al. ............................. 623/20 |
| 4,634,444 | 1/1987 | Noiles .................................... 623/20 |
| 4,728,332 | 3/1988 | Albrektsson .......................... 623/20 |
| 4,888,021 | 12/1989 | Forte et al. ............................ 623/20 |
| 4,950,297 | 8/1990 | Elloy et al. ............................ 623/20 |
| 5,011,496 | 4/1991 | Forte et al. ............................ 623/20 |
| 5,080,675 | 1/1992 | Lawes et al. .......................... 623/20 |
| 5,171,283 | 12/1992 | Pappas et al. ......................... 623/20 |
| 5,282,868 | 2/1994 | Bahler .................................... 623/20 |
| 5,314,481 | 5/1994 | Bianco ................................... 623/20 |
| 5,314,483 | 5/1994 | Wehrli et al. .......................... 623/20 |
| 5,330,533 | 7/1994 | Walker ................................... 623/20 |
| 5,344,460 | 9/1994 | Turanyi et al. ........................ 623/20 |
| 5,358,527 | 10/1994 | Forte ...................................... 623/20 |
| 5,358,530 | 10/1994 | Hodorek ................................ 623/20 |
| 5,358,531 | 10/1994 | Goodfellow et al. .................. 623/20 |
| 5,370,701 | 12/1994 | Finn ....................................... 623/20 |
| 5,387,240 | 2/1995 | Pottenger et al. ..................... 623/20 |
| 5,395,401 | 3/1995 | Bahler ................................... 623/20 |
| 5,413,604 | 5/1995 | Hodge .................................... 623/20 |
| 5,413,608 | 5/1995 | Keller .................................... 623/20 |
| 5,458,644 | 10/1995 | Grundei ................................. 623/20 |
| 5,480,446 | 1/1996 | Goodfellow et al. .................. 623/20 |
| 5,549,689 | 8/1996 | Epstein et al. ......................... 623/20 |
| 5,556,432 | 9/1996 | Kubein-Meesenburg et al. .... 623/20 |
| 5,609,639 | 3/1997 | Walker ................................... 623/20 |
| 5,609,644 | 3/1997 | Ashby et al. .......................... 623/20 |
| 5,658,342 | 8/1997 | Draganich et al. .................... 623/20 |
| 5,683,468 | 11/1997 | Pappas ................................... 623/20 |
| 5,702,466 | 12/1997 | Pappas et al. ......................... 623/20 |
| 5,725,584 | 3/1998 | Walker et al. ......................... 623/20 |
| 5,879,394 | 3/1999 | Ashby et al. .......................... 623/20 |
| 6,123,728 * | 9/2000 | Brosnahan et al. ............... 623/20.24 |

FOREIGN PATENT DOCUMENTS

| | | | |
|---|---|---|---|
| 0 636 353 A1 | 2/1995 | (EP) | ................................. A61F/2/38 |
| 0 674 887 A1 | 3/1995 | (EP) | ................................. A61F/2/38 |
| 79.20563 | 8/1979 | (FR) | ................................. A61F/1/00 |
| 2 277 034 B | 10/1994 | (GB) | ................................. A61F/2/38 |
| 2 278 782 A | 12/1994 | (GB) | ................................. A61F/2/38 |
| 2 280 375 B | 2/1995 | (GB) | ................................. A61F/2/38 |
| 2 291 355 B | 7/1995 | (GB) | ................................. A61F/2/38 |
| 2 293 109 A | 3/1996 | (GB) | ................................. A61F/2/38 |
| 2 304 051 A | 3/1997 | (GB) | ................................. A61F/2/38 |
| 2 312 166 A | 10/1997 | (GB) | ................................. A61F/2/38 |
| 2 312 167 A | 10/1997 | (GB) | ................................. A61F/2/38 |
| 2 312 168 A | 10/1997 | (GB) | ................................. A61F/2/38 |
| 2 312 377 A | 10/1997 | (GB) | ................................. A61F/2/38 |
| 2 313 314 A | 11/1997 | (GB) | ................................. A61F/2/38 |
| WO 95/22303 | 8/1995 | (WO) | ................................. A61F/2/38 |
| WO 95/25484 | 9/1995 | (WO) | ................................. A61F/2/38 |
| WO 95/27450 | 10/1995 | (WO) | ................................. A61F/2/38 |
| WO 95/30390 | 11/1995 | (WO) | ................................. A61F/2/38 |
| WO 96/01087 | 1/1996 | (WO) | ................................. A61F/2/38 |
| WO 96/03097 | 2/1996 | (WO) | ................................. A61F/2/38 |

OTHER PUBLICATIONS

The Sliding Meniscus Knee Prosthesis: Design Concepts; R. J. Minns, J. Campbell.

The Design and BioMechanics of a Sliding Mensicus Knee Prosthesis; R. J. Minns; pp 306–309.

The Oxford Meniscal Knee Phase II; Biomet Ltd.; British JBJS, May 1998.

New Jersey Tricompartmental Total Knee System with Porocoat Surgical Procedure; Frederick F. Buechel, M.D.; DePuy.

New Jersey LCS™ Total Knee System with Porocoat; DePuy; JBJS vol. 67–A, No. 8; Oct. 1985.

AGC Total Knee System; Biomet Ltd., British JBJS; Nov. 1985.

Minns Meniscal Knee—A Total Prosthesis for Early Joint Degeneration; Zimmer (Swindon).

Gliding Meniscal Knee—A Major Development in Cruciate–Retaining Arthroplasty; Zimmer (Swindon).

Longer Implant Life in Three Easy Lessons; JBJS—Jul. 1998; DePuy.

SAL. Self–Aligning. An Evolution in Motion; Protek; JBJS Oct. 1997.

In 1977, The LCS™ Changed the Way Knee Work; Brit JBJS, Mar. 1997; DePuy.

Study the Facts—The Oxford™ Knee; British JBJS Mar. 1998; Biomet Ltd.

* cited by examiner

TIBIAL KNEE COMPONENT WITH A MOBILE BEARING

BACKGROUND OF THE INVENTION

1. Field of the Invention

The present invention relates to an orthopaedic implant, and, more particularly, to a tibial knee component.

2. Description of the Related Art

A tibial knee component is implanted within a proximal tibia and engages with a femoral component implanted within a distal femur. The tibial knee component typically includes a bearing which is fixed to a tibial tray. The tibial tray may include a stem which is implanted within the intramedullary (IM) canal in the proximal tibia. The bearing may be in the form of a low friction material highly resistant to wear such as ultra high molecular weight polyethylene (UHMWPE) which is fixed to the tibial tray. Articular movement between the femoral component and the bearing surface of the bearing occurs with relatively low friction and wear characteristics.

It is also known to provide a mobile bearing which moves to a limited extent relative to the tibial tray. During deep flexion between the femur and tibia, the bearing rotates to a limited extent about a longitudinal axis associated with a pivot point at the attachment location between the bearing and tibial tray. Although known designs are adequate to allow limited rotation between the bearing and tibial tray, they may be relatively complex and thus expensive to manufacture.

What is needed in the art is a tibial knee component with a mobile bearing which is easier to manufacture and still allows adequate movement between the bearing and tibial tray during deep flexion of the knee joint.

SUMMARY OF THE INVENTION

The present invention provides a tibial knee component with a tibial tray having a cylindrical projection which is received within a cylindrical opening of a bearing. The bearing may be further attached to the tibial tray using a bolt to inhibit axial movement thereof, and may include a vent hole in fluid communication with the opening for allowing a fluid to escape from the opening. The bearing has a backing surface which is substantially entirely supported by the tibial tray, regardless of the relative positioning between the bearing and tibial tray.

The invention comprises, in one form thereof, an orthopaedic knee component for implanting within a proximal tibia. A tibial tray includes a proximal tibial plateau with a projection extending generally orthogonal to the tibial plateau. The tibial tray also includes a distally extending stem. A bearing is coupled with the tibial plateau and has an articular bearing surface for engagement with a femoral component. The bearing is rotationally movable between a first rotational limit and a second rotational limit about an axis extending generally orthogonal to the tibial plateau. The bearing has a backing surface engaging the tibial plateau which is sized and shaped such that the backing surface is substantially entirely supported by the tibial plateau at any position during rotational movement between the first rotation limit and the second rotational limit.

The invention comprises, in another form thereof, an orthopaedic knee component for implanting within a proximal tibia. A tibial tray includes a proximal tibial plateau, a projection extending generally orthogonal from the tibial plateau and defining an axis of rotation, and a distally extending stem. A bearing is carried by the tibial tray and has an opening in which the projection is disposed. The opening and the projection allow rotational movement of the bearing relative to the tibial plateau about the axis. The bearing has an articular bearing surface for engagement with a femoral component. The bearing further has a vent hole in fluid communication with the opening.

An advantage of the present invention is that substantially all of the bearing backing surface is supported by the tibial plateau at any rotational position.

Another advantage is that the bearing is provided with a vent hole which allows air to escape from the opening when the projection is inserted therein during assembly, and allows bodily fluid to escape from the opening after implantation.

Yet another advantage is that a fastener such as a bolt may be used to further fasten the bearing to the tibial tray, effectively extending the length of the projection and preventing lift off of the bearing during deep flexion of the knee.

A further advantage is that the tibial tray and bearing are provided with a post and notch configuration, respectively, to limit the rotational movement of the bearing relative to the tibial tray.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 3:
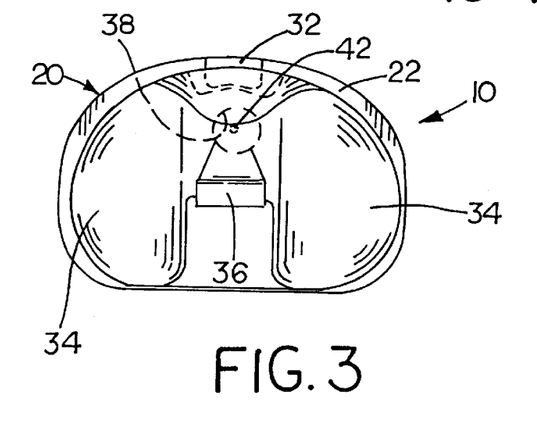
FIG. 3 is a top view of the orthopaedic knee component of FIGS. 1 and 2, with the bearing located at a neutral position.
Figure 4:
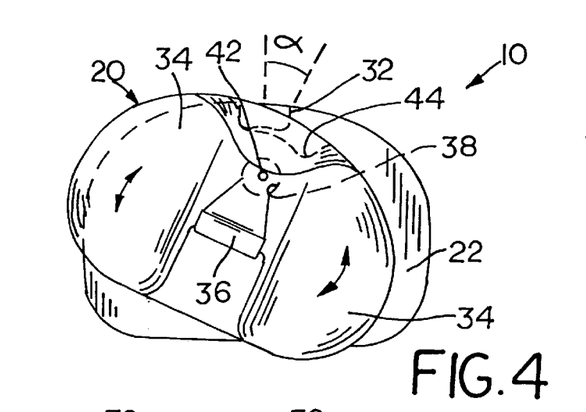
FIG. 4 is a top view of the orthopaedic knee component of FIGS. 1–3, with the bearing in a rotated position.
Figure 5:
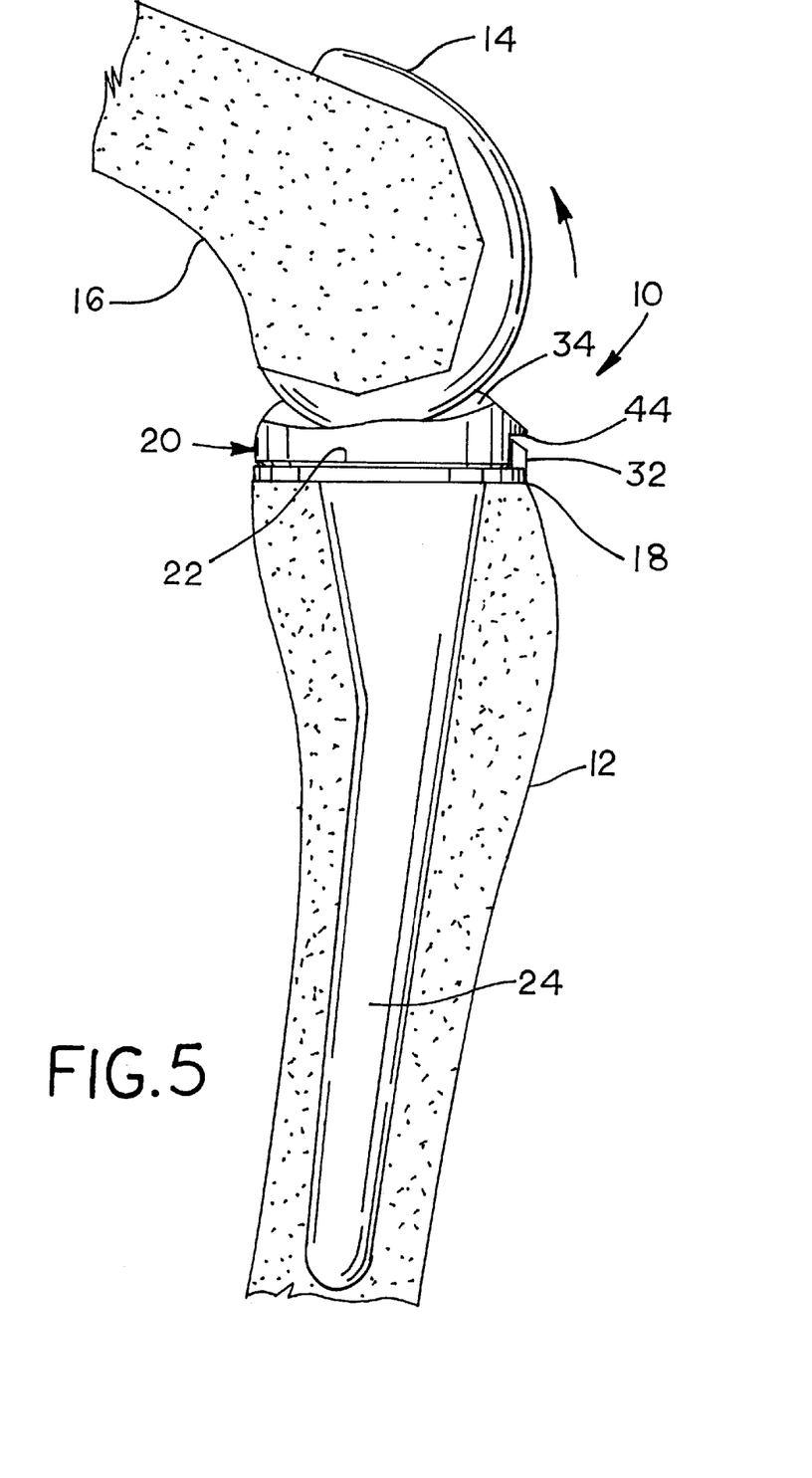
FIG. 5 is a side view of the orthopaedic knee component of FIGS. 1–4, implanted within a tibia and engaged with a femoral component.
Figure 6:
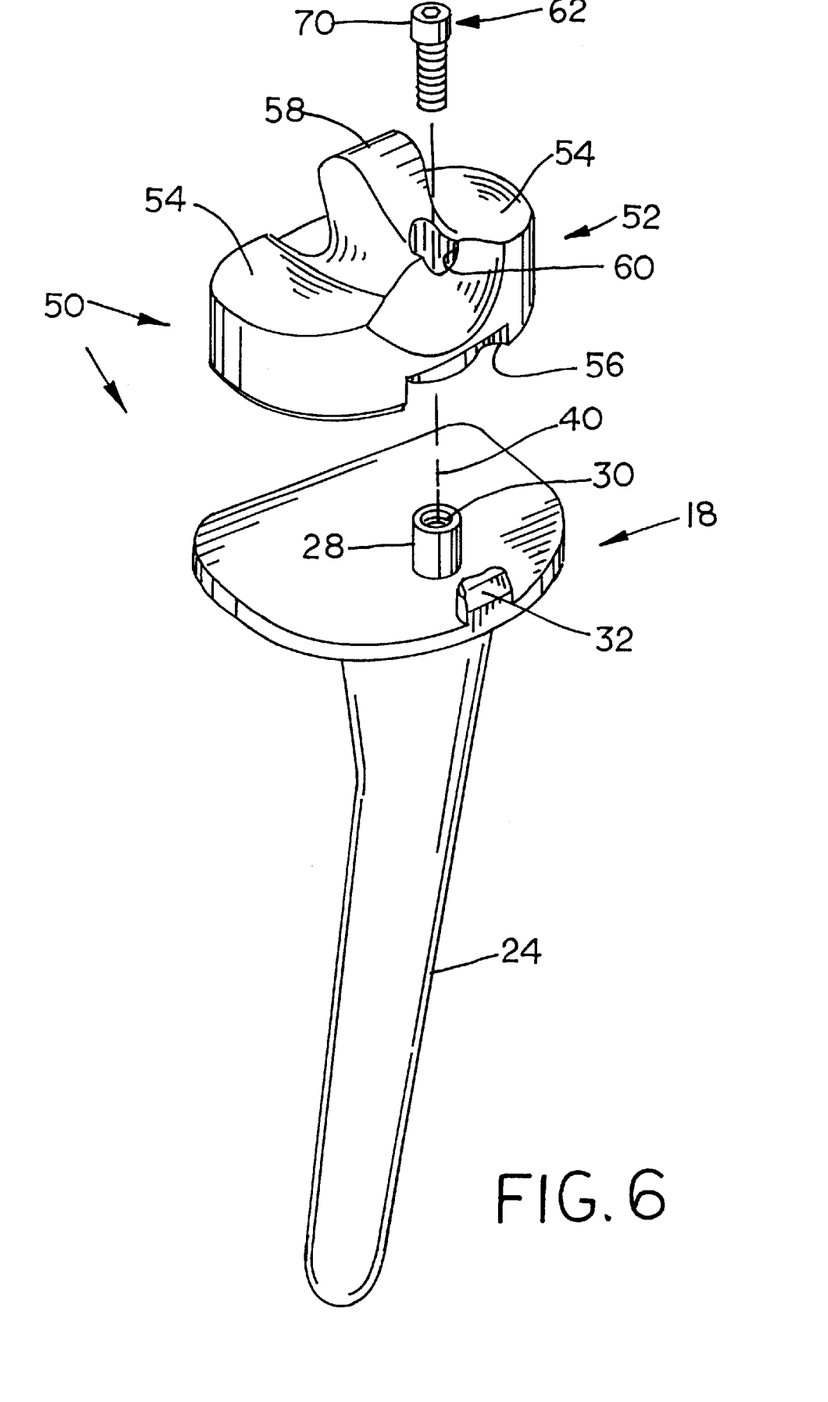
FIG. 6 is an exploded, perspective view of another embodiment of an orthopaedic knee component of the present invention.
Figure 7:
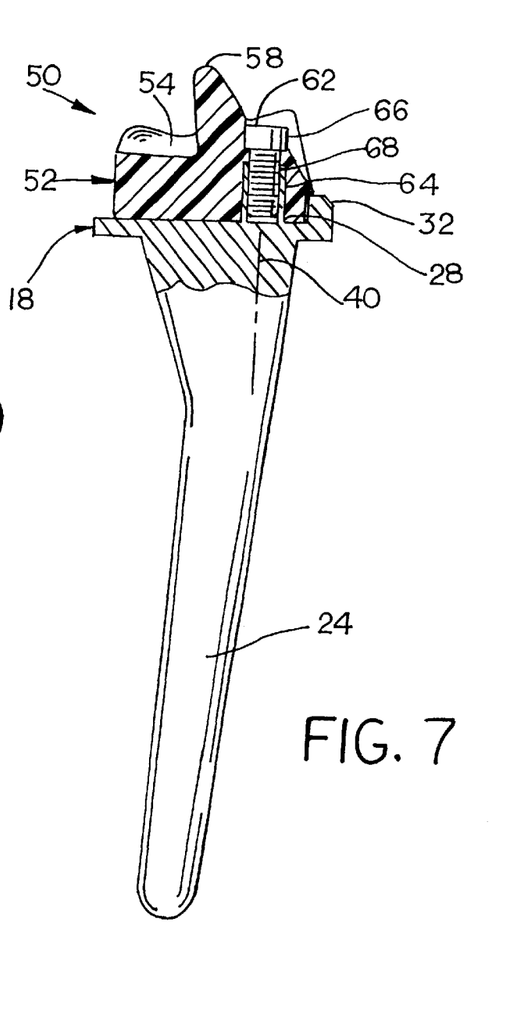
FIG. 7 is a side, partially sectioned view of the orthopaedic knee component of FIG. 6.
Figures 8, 9:
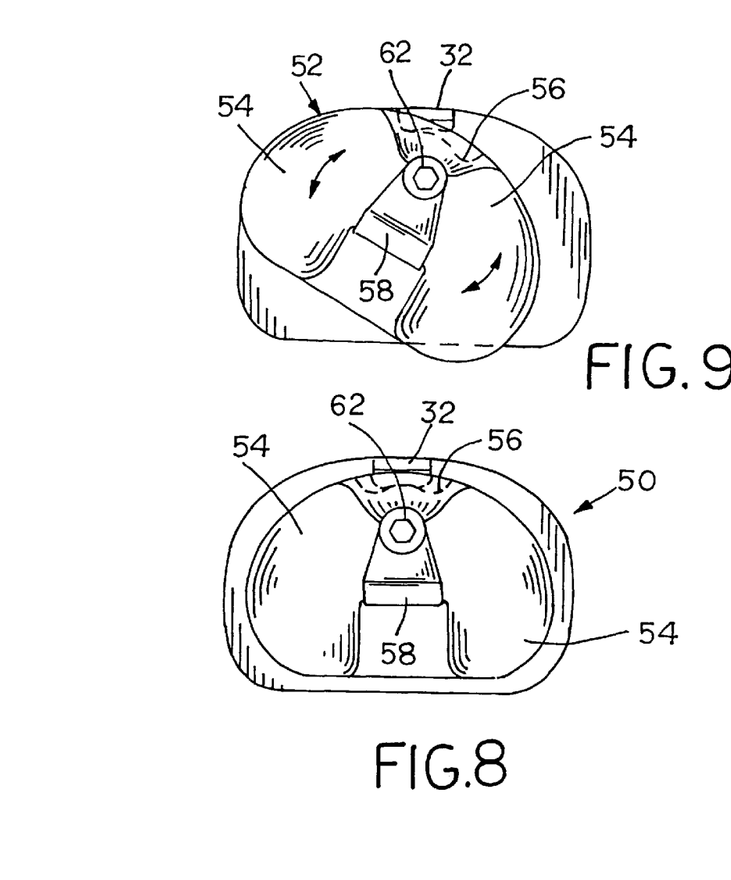
FIG. 8 is a top view of the orthopaedic knee component of FIGS. 6 and 7, with the bearing in a neutral position.
FIG. 9 is a top view of the orthopaedic knee component of FIGS. 6–8, with the bearing in a rotated position.
Figure 10:
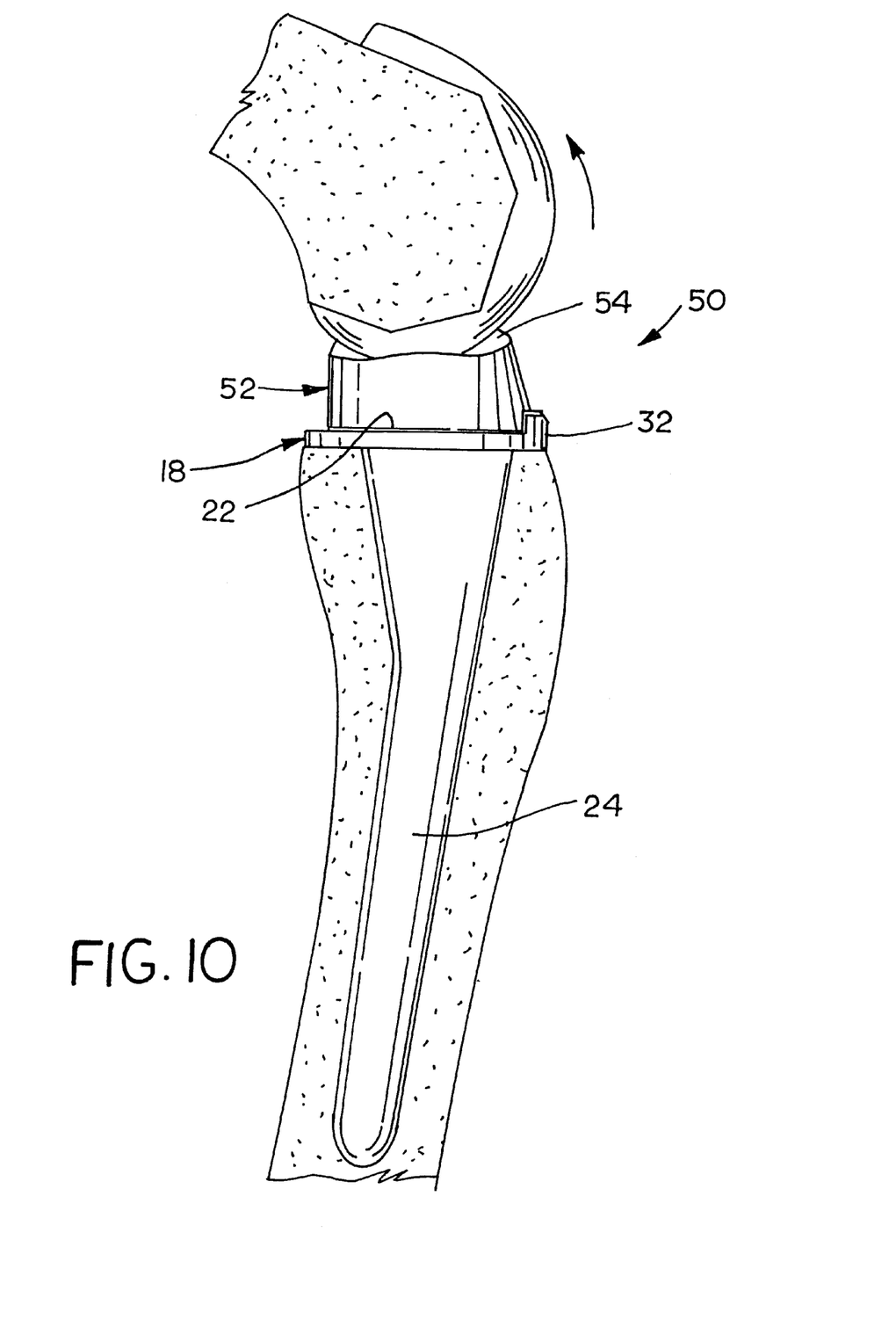
FIG. 10 is a side view of the orthopaedic knee component of FIGS. 6–9, implanted within a tibia and engaged with a femoral component.

Referring now to the drawings, and more particularly to FIGS. 1–5, there is shown an embodiment of an orthopaedic knee component in the form of a tibial knee component 10 which is implanted within a proximal tibia 12 (FIG. 5). Tibial knee component 10 engages with a femoral knee component 14 which is implanted within a distal femur 16.

Figure 1:
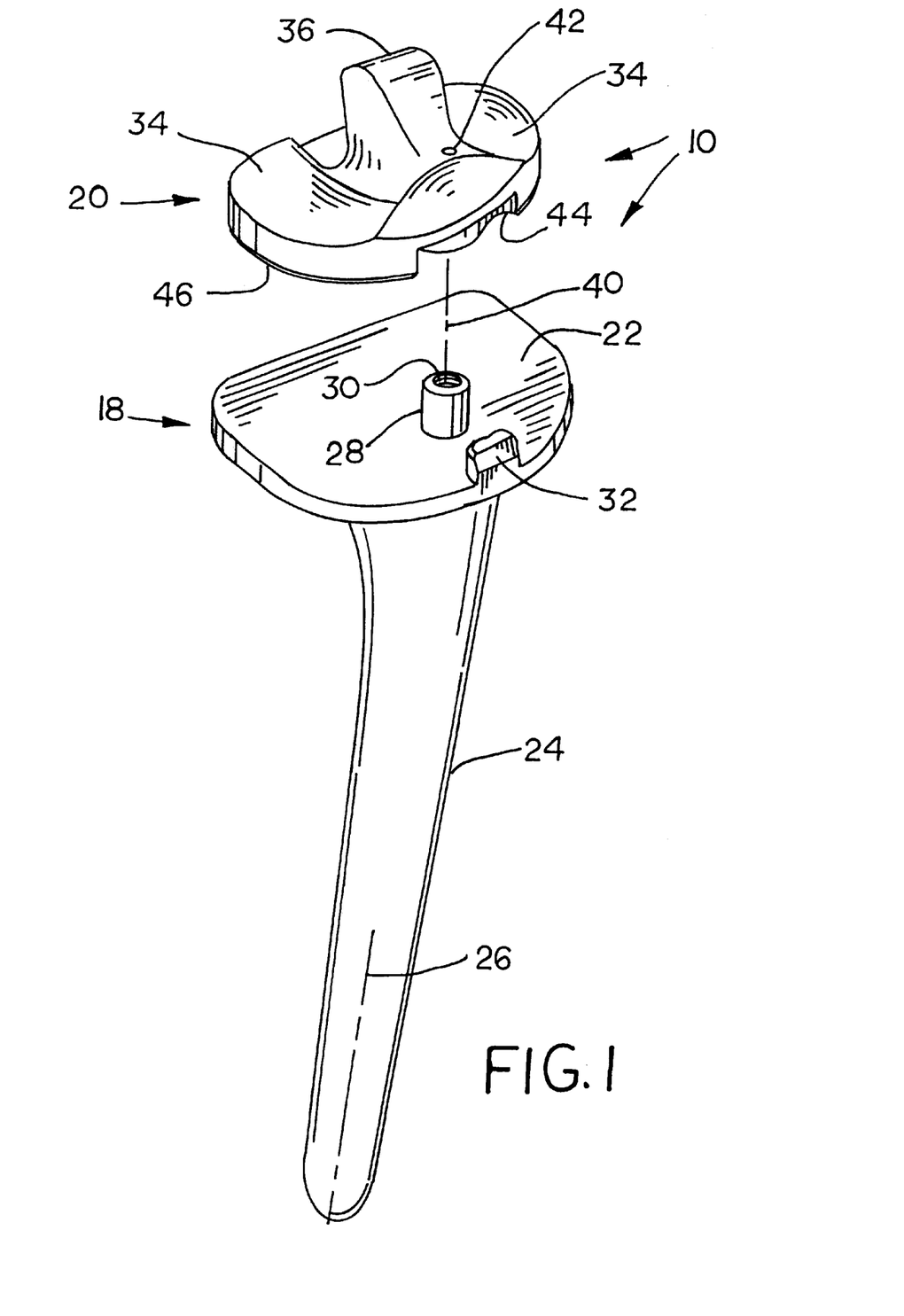
FIG. 1 is an exploded, perspective view of an embodiment of an orthopaedic knee component of the present invention.
Figure 2:
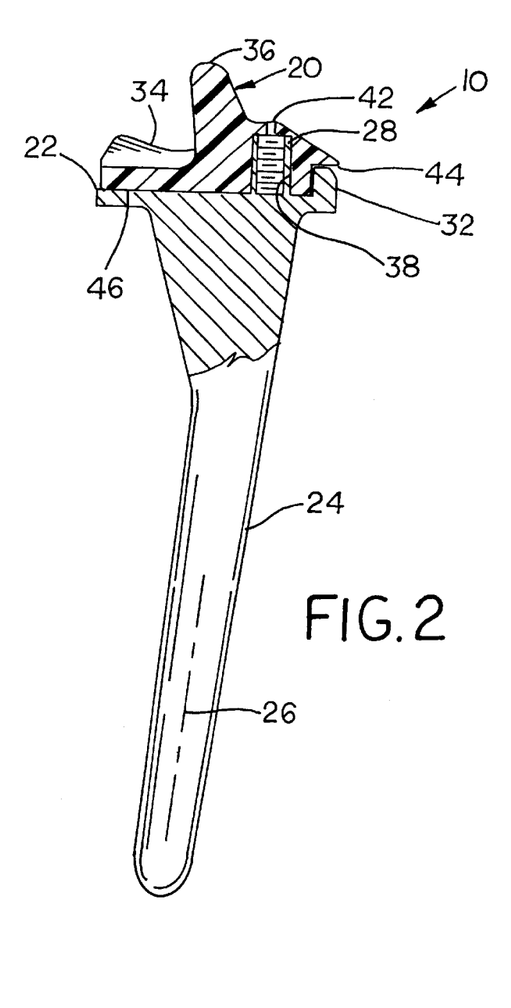
FIG. 2 is a side, partially sectioned view of the orthopaedic knee component of FIG. 1.

Tibial knee component 10 includes a tibial tray 18 and a bearing 20. Tibial tray 18 has a proximal tibial plateau 22 and a distally extending stem 24. Tibial plateau 22 has a generally planar proximal surface which extends transverse (e.g., orthogonal) to a longitudinal axis 26 of stem 24. A generally cylindrical shaped projection 28 has an internally threaded hole 30 which will be described in more detail hereinafter. Projection 28 has an axis of rotation 40 which extends generally orthogonal to tibial plateau 22.

Tibial tray 18 also includes a post 32 which extends from tibial plateau 22. Post 32 provides a rotational stop when tibial tray is engaged with bearing 20, as will be described in more detail hereinafter. Post 32 may have any suitable configuration. In the embodiment shown, post 32 has a surface which faces toward bearing 20 and includes two rounded shoulders to inhibit wear between post 32 and bearing 20 at the rotational limits of bearing 20.

Bearing 20 has an articular bearing surface 34 for engagement with femoral component 14. Articular bearing surface 34 is disposed on either side of a center projection 36. Each discrete portion of articular bearing surface 34 on either side of projection 36 engages a corresponding condyle of femoral knee component 14, with projection 36 being disposed between the condyles.

Bearing 20 also includes a generally cylindrical shaped opening 38 in which projection 28 is disposed. Opening 38 and projection 28 allow rotational movement of bearing 20 relative to tibial plateau 22 about axis of rotation 40 of projection 28. Opening 38 has a diameter which is just slightly larger than an outside diameter of projection 28, such that movement of bearing 20 in a generally radial direction relative to axis 40 is inhibited. A vent hole 42 with a diameter which is smaller than a diameter of opening 38 is positioned generally concentric with opening 38. Vent hole 42 prevents a pressure build up within opening 38 that might tend to cause bearing 20 to move in an axial direction away from projection 28. For example, when projection 28 is placed into opening 38 of bearing 20 during assembly, vent hole 42 allows air to escape through to the ambient environment. Additionally, after tibial knee implant 10 is implanted, bodily liquid may seep into opening 38 on the proximal side of projection 28 as a result of capillary action, etc. thus during use, a pressure build up may occur between tibial plate 18 and bearing 20 at the junction between projection 28 and opening 38 which may cause the bearing to be pushed out of contact with plate 18. Therefore, vent hole 42 allows the bodily fluid to flow from opening 38 without a buildup of pressure.

Bearing 20 also includes a notch 44 in which post 32 is received. Notch 44 has a surface facing post 32 with a curvature corresponding to the curvature of post 32 and the radius of curvature relative to the distance to axis of rotation 40. Notch 44 and post 32 allow rotational movement of bearing 20 between a first rotational limit and a second rotational limit about axis of rotation 40. Bearing 20 is shown in FIG. 4 at a first rotational limit which is approximately 25° relative to a neutral or symmetric position shown in FIG. 3. Thus, bearing 20 is rotationally movable through an angle 2α of approximately 50° between the first rotational limit and the second rotational limit (in a direction opposite to that shown in FIG. 4).

Bearing 20 has a backing surface 46 which engages with tibial plateau 22. Backing surface 46 is generally planar to match the corresponding generally planar configuration of tibial plateau 22. Backing surface 46 defines a load bearing surface with tibial plateau which transfers the load imparted either by the femoral condyles engaging articular bearing surface 34. Backing surface 46 is sized and configured such that backing surface 46 is substantially entirely supported by tibial plateau 22 at any position during rotational movement between the first rotational limit and the second rotational limit. As illustrated in FIG. 3, backing surface 46 of bearing 20 is entirely supported by tibial plateau 22 when bearing 20 is at a neutral position. Similarly, backing surface 46 is substantially entirely supported by tibial plateau 22 when bearing 20 is at a first rotational limit (FIG. 4), a second rotational limit, or any position therebetween.

With a conventional tibial knee component, the tibial tray includes a notch on the posterior side such that the tibial plateau has a generally U-shape when viewed in a proximal-distal direction. Moreover, the bearing may overhang the tibial tray by a substantial amount when the bearing is at a rotational limit. On the other hand, tibial plateau 22 of the present invention does not include a notch on the posterior side and the bearing does not overhang the tibial plateau by any appreciable amount when at a first rotational limit or a second rotational limit. Thus, bearing 20 is better supported to reduce the potential for implant deformation due to excessive overhang between backing surface 46 and tibial plateau 22 is reduced.

FIGS. 6–10 illustrate another embodiment of an orthopaedic knee component in the form of a tibial knee component 50 of the present invention. Tibial knee component 50 includes a bearing 52 which is similar in many respects to bearing 20 shown in FIGS. 1–5. Bearing 52 is attached with tibial tray 18 shown in FIGS. 1–5.

Bearing 52 includes an articular bearing surface 54, notch 56 and projection 58 similar to articular bearing surface 34, notch 44 and projection 36 shown in the embodiment of tibial knee component 10 illustrated in FIGS. 1–5. Moreover, bearing 52 includes a generally cylindrical shaped opening 60 which has a diameter slightly larger than projection 28 and receives projection 28 therein. However, bearing 52 has a thickness in the proximal-distal direction which is much thicker than bearing 20 shown in FIGS. 1–5. To ensure that bearing 52 does not lift off of projection 28 during deep flexion of the knee joint, a fastener in the form of a shoulder bolt 62 extends through opening 60 and threadingly engages with internally threaded hole 30 of projection 28. Opening 60 includes a first diameter 64 which is just slightly larger than the diameter of projection 28, and a second diameter 66 which defines a shoulder 68. Head 70 does not tighten against shoulder 68 such that bearing 52 is free to pivot about axis of rotation 40. A small clearance distance also exists between bolt head 70 and second diameter 66 such that opening 60 likewise defines a vent hole for allowing a fluid such as air or a bodily liquid to exit therefrom.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic knee component for implanting within a proximal tibia, comprising:
   a tibial tray including a proximal tibial plateau with a projection extending generally orthogonal to said tibial plateau;
   a bearing coupled with said tibial plateau and having an articular bearing surface for engagement with a femoral component, said bearing being rotationally movable between a first rotational limit and a second rotational limit about an axis extending generally orthogonal to said tibial plateau, said bearing having a backing surface engaging said tibial plateau which is sized and shaped such that said backing surface is substantially entirely supported by said tibial plateau at any position during said rotational movement between said first rotational limit and said second rotational limit; and
   said tibial tray including a post extending from said tibial plateau, said bearing including a notch in which said post is received, said post and said notch limiting said rotational movement of said bearing between said first rotational limit and said second rotational limit.

2. The orthopaedic knee component of claim 1, wherein said notch extends from said backing surface.

3. The orthopaedic knee component of claim 1, wherein said bearing is rotationally movable through an angle of approximately 50° between said first rotational limit and said second rotational limit.

4. An orthopaedic knee component for implanting within a proximal tibia, comprising:
   a tibial tray including a proximal tibial plateau, a projection extending generally orthogonal from said tibial plateau and defining an axis of rotation; and
   a bearing carried by said tibial tray and having an opening in which said projection is disposed, said opening and said projection allowing rotational movement of said bearing relative to said tibial plateau about said axis of rotation, said bearing having an articular bearing surface for engagement with a femoral component, said bearing further having a vent hole in fluid communication with said opening.

5. The orthopaedic knee component of claim 4, wherein each of said projection and said opening are generally cylindrical shaped.

6. The orthopaedic knee component of claim 4, wherein said opening in said bearing substantially inhibits movement of said bearing relative to said tibial plateau in a generally radial direction relative to said axis.

7. The orthopaedic knee component of claim 4, wherein said vent hole has a diameter which is smaller than a diameter of said opening.

8. The orthopaedic knee component of claim 4, wherein said vent hole extends generally parallel to said axis.

9. An orthopaedic knee component for implanting within a proximal tibia, comprising:
   a tibial tray including a proximal tibial plateau, a projection extending generally orthogonal from said tibial plateau and defining an axis of rotation;
   a bearing carried by said tibial tray and having an opening in which said projection is disposed, said opening and said projection allowing rotational movement of said bearing relative to said tibial plateau about said axis, said bearing having an articular bearing surface for engagement with a femoral component, said opening including a first diameter corresponding to a diameter of said projection and a second diameter defining a shoulder; and
   a fastener extending through said opening and attached with said projection, said fastener seating against said shoulder, said fastener inhibiting movement of said bearing relative to said tibial plateau in a direction generally parallel to said axis of rotation.

10. The orthopaedic knee component of claim 9, wherein said fastener comprises a bolt with a head which seats against said shoulder.

11. The orthopaedic knee component of claim 10, wherein said bolt head is recessed within said opening.

12. The orthopaedic knee component of claim 9, wherein said projection includes a female threaded hole, and said fastener comprises a bolt.

* * * * *